United States Patent [19]
Lobo et al.

[11] Patent Number: 4,861,167
[45] Date of Patent: Aug. 29, 1989

[54] LINE-HEAT-SOURCE THERMAL CONDUCTIVITY MEASURING SYSTEM

[75] Inventors: Hubert Lobo; Kuo K. Wang, both of Ithaca, N.Y.

[73] Assignee: Cornell Research Foundation, Inc., Ithaca, N.Y.

[21] Appl. No.: 250,406

[22] Filed: Sep. 28, 1988

[51] Int. Cl.[4] .......................................... G01N 25/18
[52] U.S. Cl. .................................... 374/44; 374/12; 374/33; 374/143; 364/557
[58] Field of Search ....................... 374/12, 31, 33, 36, 374/38, 43, 44, 143; 364/557

[56] References Cited

U.S. PATENT DOCUMENTS

| | | | |
|---|---|---|---|
| 3,592,060 | 7/1971 | Laverman | 374/43 |
| 3,677,294 | 6/1972 | Schoenlaub | 374/33 |
| 4,059,982 | 11/1977 | Bowman | 374/44 |

FOREIGN PATENT DOCUMENTS

| | | | |
|---|---|---|---|
| 55-124051 | 9/1980 | Japan | 374/43 |
| 57-23846 | 2/1982 | Japan | 374/43 |
| 60-36944 | 2/1985 | Japan | 374/44 |
| 60-231147 | 11/1985 | Japan | 374/44 |
| 8402598 | 3/1986 | Netherlands | 374/44 |
| 840722 | 6/1981 | U.S.S.R. | 374/44 |
| 2198238 | 6/1988 | United Kingdom | 374/44 |

OTHER PUBLICATIONS

Sweat, V. E, and Huggins, L. F., "Automation of a Miniature Thermal Conductivity Probe", Conference: Advances in Thermal Conductivity, Lake Ozark, MO (Nov. 5-7 1974), pp. 318-324.

Hands, D.,and Horsfall, F., "A Thermal Conductivity Apparatus for Solid and Molten Polymers", Journal of Physics E, vol 8, No. 8, pp. 687-690, Aug. 1975.

Katayama, K. et al., "A New Method of Simultaneous Measurement of Several Thermal Properties by Continuous Heating", Heat Transfer–Japanese Research, vol. 1, No. 1 (Jan.–Mar. 1972).

ASTM D 2326-64T, "Thermal Conductivity of Cellular Plastics by Means of a Probe", 1965 Book of ASTM Standards, pp. 473-477.

Hoshi, M. et al., "Transient Method to Measure the Thermal Conductivity of High–Temperature Melts Using a Liquid–Metal Probe", Rev. Sci. Instrum. 52(5), pp. 755-758, May 1981.

*Primary Examiner*—William A. Cuchlinski, Jr.
*Assistant Examiner*—Diego F. F. Gutierrez
*Attorney, Agent, or Firm*—Jones, Tullar & Cooper

[57] ABSTRACT

An apparatus and method for measurement of the thermal conductivity of polymer melts is disclosed. A sample of material to be measured is placed in an elongated cylindrical container and is heated to a preselected base temperature. A probe placed in the container in contact with the sample contains a transient heating element and a temperature sensor. To determine the thermal conductivity of the sample material, the transient heating element is energized and the resulting changing temperature of the sample material is measured for a short period of time. The rate of temperature change is a measure of the thermal conductivity of the sample material at the base temperature.

22 Claims, 5 Drawing Sheets

LINE-HEAT-SOURCE THERMAL CONDUCTIVITY MEASURING SYSTEM

BACKGROUND OF THE INVENTION

The present invention relates, in general, to apparatus and a method for the measurement of thermal conductivity of materials, and more particularly to the measurement of the thermal conductivity of polymer melts, rubber, and blends of materials at high temperature and pressures.

The measurement of thermal conductivity of materials has always been a difficult problem, with a great deal of uncertainty in the measurement. This is mainly due to factors, such as thermal contact resistance, heat losses, and heat capacity of the probe materials, which cannot be accounted for easily. Steady-state methods, because of their simple governing equations, are considered to be more accurate than the transient methods and have been adopted as the ASTM standard.

Polymer melts belong to a class of materials of intermediate thermal conductivity. Commercial polymer melts need to be measured for thermal conductivity at typical processing temperatures in the range of 150° to 350° C. No thermal conductivity standard has been established to date for this class of materials, and available data is inconsistent and sketchy. This is mainly because, until now, most workers have relied on the conventional "guarded hot plate" steady state device which is the ASTM standard. This apparatus is cumbersome, requires extensive sample preparation, and can take from four to twenty-four hours to reach steady state. While well worth the effort for most materials other than polymer melts, because of its accuracy, it is quite useless for polymer melts because the characteristics of these materials change, due to degradation, when exposed to high melt temperatures for extended periods of time. Also, handling molten polymers in this type of apparatus can be difficult, messy, and often hazardous. Thus, there is a need for an apparatus which will facilitate the handling of molten polymer materials and which will, at the same time, permit the measurement of thermal conductivity accurately and quickly, without the need for long-term heating to temperatures which can degrade the material being measured.

Line-source methods which measure the transient flow of heat in cylindrical geometries have been developed, and such methods, which are related in principle to hot-wire methods, have found wide application in measurements of soils, foods, and materials whose properties change with time. The line-source method has been used for measurements on polystyrene and polyethylene in the 20° to 180° C. temperature range. However, such apparatus has been inconvenient to use because the measurement and heater wires required for such an apparatus were embedded directly in the sample, necessitating the use of new wires for each experiment. This placed an additional degree of uncertainty to the measurement, because reproducibility could not be assured.

SUMMARY OF THE INVENTION

Briefly, the present invention overcomes the problems of the prior art by providing a method of measuring thermal conductivity through the use of a measuring probe which includes conventional heater wires and a thermocouple encased in a stainless steel sheath or needle. The probe is used in conjunction with a barrel heater that surrounds the needle and which provides the heat required to initially melt the sample of material being tested. The probe needle is then inserted into the molten polymer material and once the temperatures of the sample and the probe equilibrate, the probe is turned on to activate its heater. The probe heater adds a small amount of heat to be probe, and the thermocouple is then used to measure the transient temperature change of the material surrounding the probe, with a multiplicity of measurements being made before the sample reaches a new steady state temperature. The probe heater is then turned off and the material is allowed to cool to its previous, or base temperature. The probe heater may then be turned on again for another cycle of measurement.

Several cycles of measurements are made in the foregoing manner, in order to obtain a reproducible measurement of the change of temperature of the sample caused by the activation of the probe heater. The transient temperature change imposed on the sample material by the activation of the probe heater is then used to calculate the thermal conductivity of the molten polymer. The use of a transient method allows a rapid, accurate, and reproducible measurement of thermal conductivity in a molten material without the need to wait for the material to reach a steady state condition. Since the line heater adds only a very small quantity of heat to the sample material, that heat dissipates quickly, allowing rapid recycling of the measurement process, minimizing the degradation of the material.

Although the use of a barrel type heater surrounding the material to be measured is preferred, in an alternative form of the invention a heating bath or an oven can be used to heat the probe and sample to a desired level, with the heater in the probe then being used to superimpose a transient temperature change on the material for measurement purposes.

BRIEF DESCRIPTION OF THE DRAWINGS

The foregoing, and additional objects, features and advantages of the present invention will become apparent to those of skill in the art from a consideration of the following detailed description of preferred embodiments thereof, taken in conjunction with the accompanying drawings, in which.

DESCRIPTION OF PREFERRED EMBODIMENTS

Figure 1:
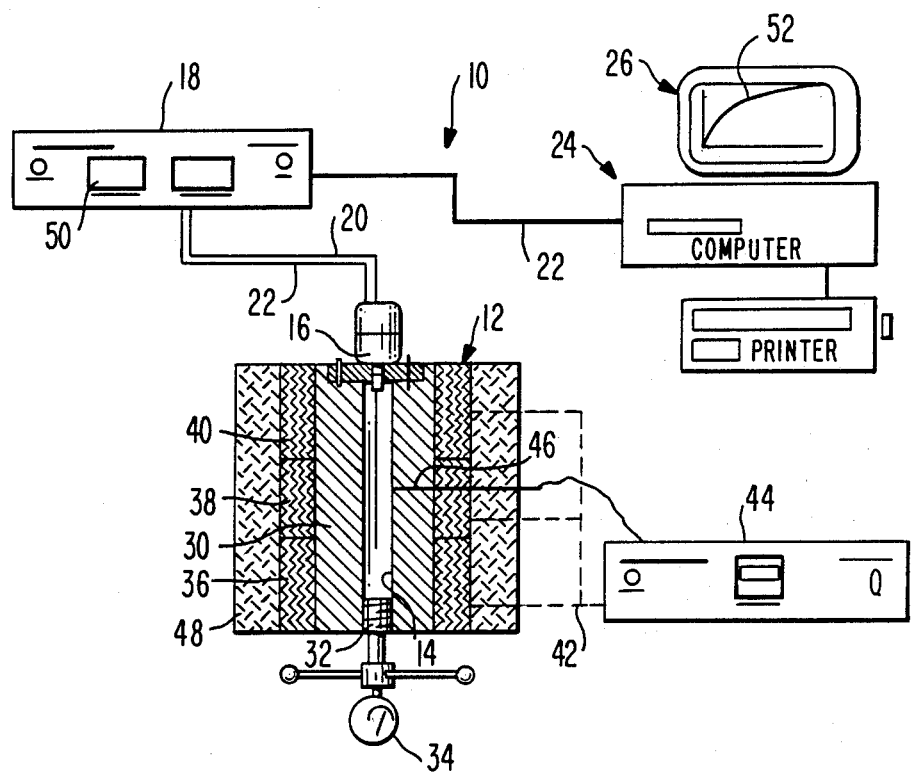
FIG. 1 is a diagrammatic view of the thermal conductivity measuring system of the present invention.

Turning now to a more detailed description of the present invention, there is illustrated in FIG. 1 a thermal conductivity measuring system generally indicated at 10 which includes a sample heater 12 for heating a material for which the thermal conductivity is to be determined. The heater includes a central cavity 14 which receives the sample material and into which a measuring probe 16 extends. The measuring probe includes a transient heater element connected to a power supply located in the probe control interface 18 by way of cable 20 and a temperature sensor connected by way of cable 22 and interface 18 to a computer 24 which records the measured temperature transient during a heating cycle and plots the measured temperature values for display on a screen 26. The computer also calculates, from the measured temperature values, the rate of change of temperature produced by the transient heater element so as to determine the thermal conductivity of the sample material.

The sample heater 12 may take the form of a barrel heater having a central metal core 30 which is cylindrical in shape and which incorporates the cavity 14. This cavity extends axially through the core 30 with an inlet end at the top of the core and an outlet end at the bottom thereof and is of constant diameter with a smooth inner surface for receiving the sample material to be tested. Plug 32 is threaded into the bottom end of the cavity 14 to close the outlet, but may be removed to permit removal of the sample material after the testing has been completed. Plug 32 may incorporate a pressure gauge 34, for high pressure measurements.

Surrounding the metal core 30 are a series of heater bands 36, 38 and 40 which are connected by way of cable 42 to a barrel temperature controller 44. Also connected to controller 44 is a temperature sensor 46 for measuring the temperature of the core 30. The controller 44 supplies electrical current to the heater bands 36, 38 and 40 to raise the temperature of the barrel heater to a selected value determined by the operator in accordance with the temperature at which the thermal conductivity of the sample material is to be determined. The controller 44 responds to the temperature measured by the sensor 46 to maintain the core temperature at the selected value. Suitable thermal insulation 48 surrounds the core.

In the operation of the system, the sample heater 12 is raised to the desired temperature and then the material to be measured is introduced into the cavity 14 through its inlet. The sample material is tamped down into the cavity to eliminate air bubbles, and the material is allowed to reach the desired base testing temperature, usually at or above the temperature at which the sample material melts. Thereafter, the probe 16 is inserted axially down the center of the cavity 14 and the temperature of the probe is monitored until it reaches the same temperature as the surrounding sample material. The temperature being measured by the probe may be displayed, for example, on a temperature display 50 on the probe control interface 18. A small constant voltage is then applied by the power supply in interface 18 to the transient heater element in the needle of probe 16 and the resulting changes in probe temperature are recorded by the computer 24. The temperature measurements are made over a relatively short period of time, before the probe reaches a steady state temperature, so that only the temperature transients are measured. Such a transient is illustrated, for example, by curve 52 on the display screen 26, and this data is then used to calculate the thermal conductivity of the material at the base temperature determined by the controller 44.

It is important that the diameter of the cavity 14 be sufficiently large that the transient heat wave produced by the transient heater element in probe 16 does not reach the wall of the heater cavity during the period of measurement. On the other hand, the diameter of the cavity should be minimized so that the initial steady state temperature determined by the controller 44 can be reached as soon as possible. A diameter of 0.8 cm has been found to be suitable.

Upon completion of the measurement of a transient produced by the heater element in the probe, the heater power is turned off and the probe is allowed to return to the temperature established by controller 44. Thereafter, a new measurement cycle may be initiated by reenergizing the probe heater element and measuring the transient response. This cycle may be repeated several times to provide reproducible results. Thereafter, the probe is removed from the sample material and the polymer is removed from the cavity 14. In the illustrated form of the invention, the polymer is removed by first removing the plug 32 at the cavity outlet and thereafter forcing the material out the bottom of the cavity by means of a manually-operated or motor-driven plunger inserted into the top of the cavity.

Figure 2:
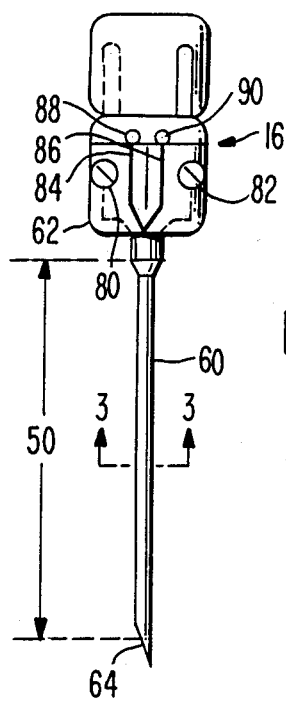
FIG. 2 is an enlarged view of a measuring probe constructed in accordance with the present invention.
Figure 3:
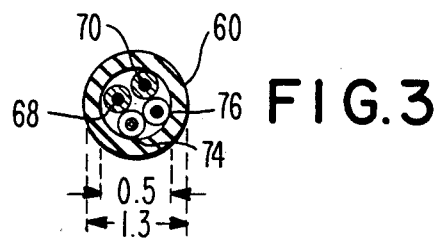
FIG. 3 is an enlarged cross sectional view taken along lines 3—3 of FIG. 2.
Figure 4:
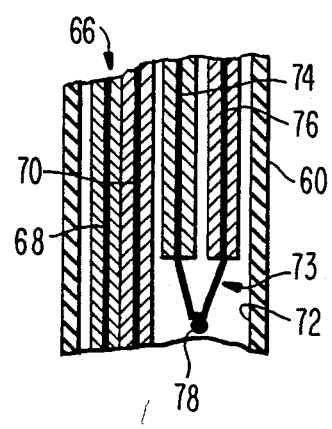
FIG. 4 is an enlarged cutaway view of a portion of the probe of FIG. 2, showing the heater wires and the thermocouple used in the probe.

Probe 16 is illustrated in greater detail in FIG. 2, and includes a needle portion 60 secured to the lower portion of a probe connector housing 62. The needle portion may be formed from a hollow, metal, preferably stainless steel, hypodermic needle which may be 50 mm long and 0.13 cm in diameter, with the tip 64 of the needle being blunted and its opening brazed shut. As illustrated in FIGS. 3 and 4, a transient heater element 66, consisting of a pair of Constantan wires 68 and 70, extends axially through the central opening of the needle which is defined by the inner wall surface 72. The heater wires, which may be about 30 gauge and insulated by a Teflon sheathing, extend substantially the entire length of the needle 60. To provide the high degree of sensitivity required for measurement of the small temperature changes produced by the transient heater element, a highly sensitive temperature sensor 73 is mounted in needle 60. Preferably, a J-Type thermocouple having a high Seebeck coefficient is used. The thermocouple is made from 30 gauge Teflon sheathed wires 74 and 76 which are spot welded together to form a bead 78. The bead is located halfway down the length of the needle portion 60 of probe 16 and is in physical contact with the inner surface 72 of the wall of needle 60. This contact is important since it minimizes the difference between the actual sample temperature and that read by the thermocouple.

The transient heater wires and the thermocouple wires are potted at the base of the hypodermic needle 60 by means of a high-temperature ceramic cement. The wires 74 and 76 are connected at their upper ends to standard thermocouple connectors 80 and 82 on the probe connector housing 62, while the transient heater wires 68 and 70 are connected by way of thick copper leads 84 and 86 to external heater wire connectors 88 and 90. Thick wires are used for the leads 84 and 86 in order to reduce heat losses outside the probe.

The power output of the transient heater within the probe 16 is too small to achieve and maintain melt temperatures, and for this reason an external source to heat the sample to its initial steady state temperature is required. The barrel-type sample heater 12 illustrated in FIG. 1 illustrates a preferred form of a conduction type heater, this type of heater being preferred because its higher transfer rate enables steady states to be reached faster. This is particularly useful for polymers that undergo rapid thermal degradation.

Figure 5:
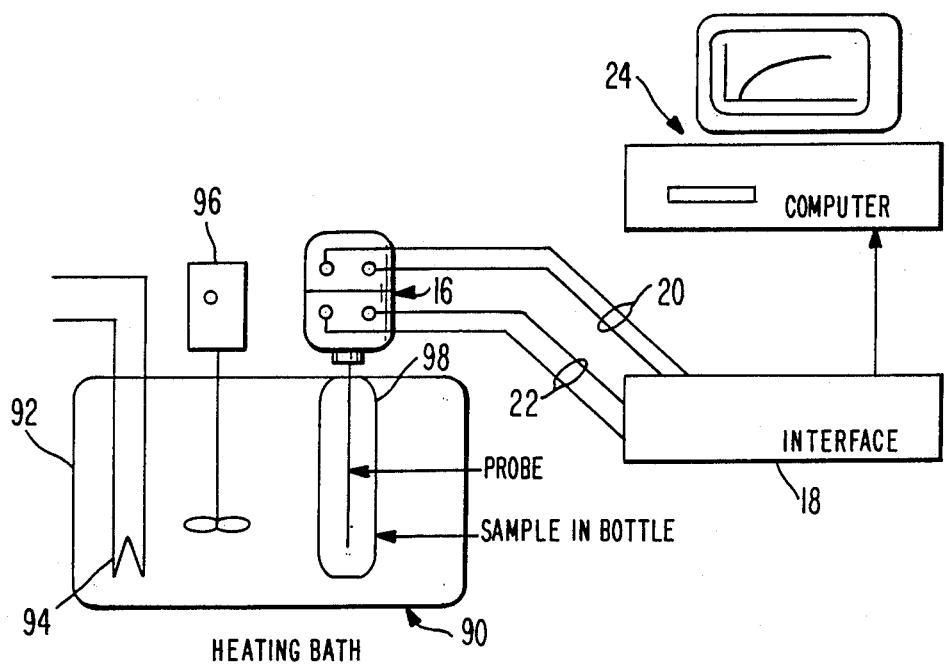
FIG. 5 is a diagrammatic view of a second embodiment of the invention.
Figure 6:
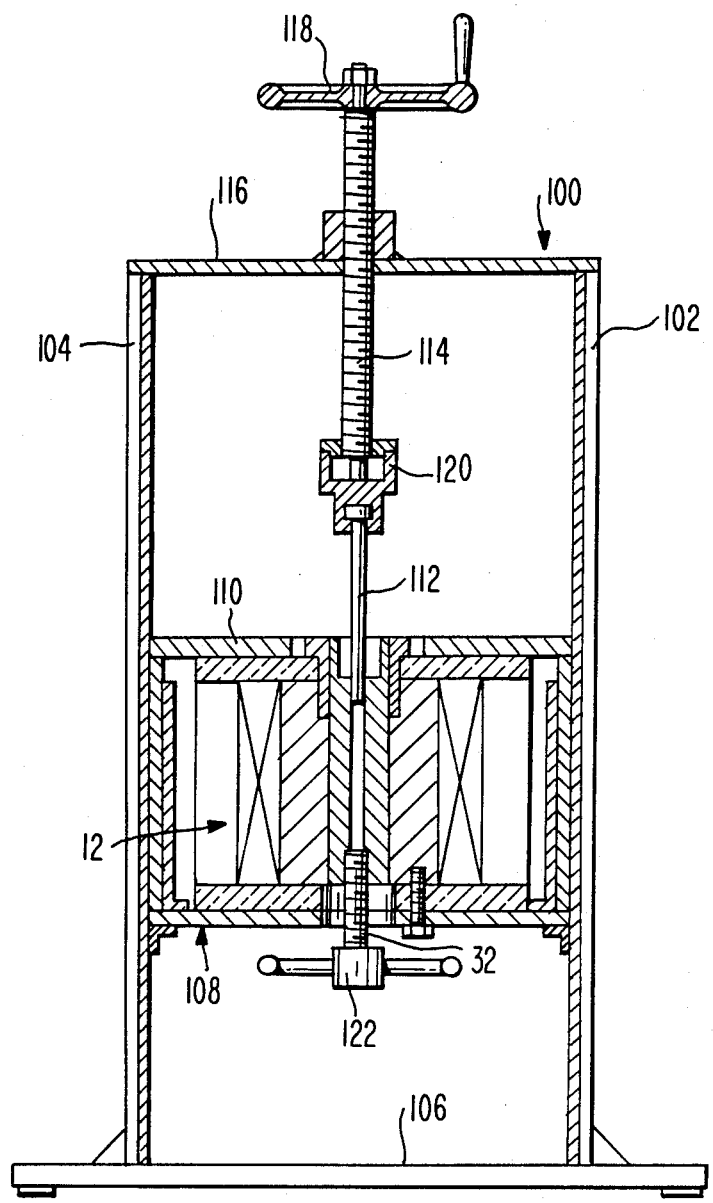
FIG. 6 is a cross sectional view of the heater barrel of FIG. 1 mounted in a loading frame for insertion of a probe into a polymer melt material.

The barrel type heater 12 is inconvenient for measurements below the melting temperature of the sample because of the difficulty in creating a homogeneous sample and because of the difficulty in purging a solidified polymer from such a heater. In cases where the sample material is reasonably stable, a circulation oil bath or fluidized sand bath system of the type illustrated at 90 in FIG. 5 may be used. An oil bath is a convenient heating medium since it can be used over a wide range of temperatures, and is especially useful for measurements that cross below the melt transition temperature of the sample. However, such a system takes longer to reach steady state and at high temperatures there is the danger of oil vapors entering the sample and altering its properties. As illustrated in FIG. 5, the bath 90 includes a housing 92 in which is received a suitable heating oil material. The oil is heated by heater elements 94 which may be connected to a temperature controller of the type illustrated at 44 in FIG. 1. A circulator pump 96 maintains an even temperature distribution throughout the bath.

The sample material for the bath system 90 is placed in a small vial 98 and for those cases where the characteristics of the sample are to be tested at temperatures below the melting temperature, the sample is melted in an oven under vacuum. The vacuum serves to minimize oxidation and air bubble formation in the sample. The probe 16 is then inserted into the molten sample, which may be a polymer, for example, and the sample is then allowed to solidify slowly to avoid shrinkage away from the probe. The sample with the embedded probe is then placed in the bath, as illustrated in FIG. 5, and after the sample has stabilized at the temperature of the oil bath, measurements of the thermal conductivity of the sample material can be made by heating the transient probe heaters by means of the power supply in the probe control interface 18 and recording the temperature transient by means of the thermocouple mounted in the probe and connected to the computer 24. As previously described, the temperature of the bath can be controlled to permit thermal conductivity readings to be taken at different sample temperatures.

As explained above, the measurements of thermal conductivity are made, in accordance with the present invention, during the time period when the temperature of the sample is changing rapidly after the probe heater is turned on. Typically, this time period will be within about 10 to 30 seconds of the time the heater is turned on so that measurements are taken of the temperature transient from the initial steady state base value established by the sample heater 12. The thermocouple provides a continuous measurement of the temperature of the sample material which surrounds and is in intimate contact with, the probe, while the computer rapidly and repeatedly samples the temperature signed from the thermocouple during this transient period in order to obtain an accurate definition of the rate of change profile of the temperature of the sample material so that an accurate determination of the thermal conductivity can be obtained.

That the foregoing measurement of the transient condition of a sample will provide an accurate measure of thermal conductivity is illustrated by the following theoretical considerations. Consider the case of a cylinder of infinite diameter and length, with an infinitesimally thin, infinitely long heating element located along its axis. The whole system is initially at constant temperature $T_0$. Starting with the Fourier conduction equation, it is possible to derive an equation for the transient temperature rise at any point in the cylinder when, starting at t=0, a constant finite quantity of heat $Q'$ is produced per unit length of the heating element. The final equation can be written:

$$T - T_0 = \frac{Q'}{2\pi k} \int_\beta^\infty \frac{e^{-u^2}}{u} du \quad \beta = \frac{r}{2\sqrt{(at)}} \quad \text{(Eq. 1)}$$

where a is the thermal diffusivity and k is the thermal conductivity of the sample, with r being the radius and t the time at which the measurement is made. The integral of equation 1 can be represented in terms of the following series expansion:

$$T - T_0 = \frac{Q'}{2\pi k}\left(-\frac{C'}{2} - \ln\beta + \frac{\beta^2}{2 \cdot 1!} - \frac{\beta^4}{4 \cdot 2!} + \cdots\right) \quad \text{(Eq. 2)}$$

where $C'$ is a constant. For values of beta less than 1/6, the integral may be represented to better than 1% accuracy by the first two terms of the series. Then, $$T - T_0 \sim \frac{Q'}{2\pi k}\{-0.2886 - \ln\beta\} \quad \text{(Eq. 3)}$$

at a fixed point at radius r, the change in temperature $(T_2 - T_1)$ in the time interval $(t_2 - t_1)$ is then given by $$T_2 - T_1 \sim \frac{Q'}{4\pi k} \ln\left(\frac{t_2}{t_1}\right) \quad \text{(Eq. 4)}$$

It is seen from the foregoing that the thermal diffusivity term is eliminated from the equation. All other terms being measurable it is then possible to calculate the thermal conductivity directly.

In order to use this approximation, it is necessary to ensure that beta is less than 1/6. It is noted that most polymers have a thermal diffusivity of the order of $10^3$ cm$^2$/sec. If r, the distance of the temperature sensor from the axis, is large it will take a long time before the above condition is satisfied. This is undesirable because a large run time necessitates large diameter samples in order to satisfy the infinite sample diameter boundary condition. This would also result in longer times being needed to reach the initial steady state condition, thereby increasing the risk of thermal degradation. By placing the temperature sensor contiguous with the heat source, as in the probe of the present invention, r tends to zero and the condition is satisfied for all values of time. The requirement for a finite sample diameter is not a problem unless the expanding transient temperature field encounters the sample boundary during the time of the measurement. In the apparatus of the present invention, for a normal run time of 10 seconds, the sample penetration depth will be of the order of 0.1 cm so that a sample diameter of about 1 cm is adequate. Further, by providing a probe with a length-to-diameter ratio greater than 20, the relative error due to axial heat flow is negligible.

As illustrated in FIG. 5, the barrel heater may conveniently be mounted in a support frame 100. The frame includes vertical side frame members 102 and 104 mounted on a base 106. The sample heater 12 is secured within a heater box 108 having a cover 110, and mounted on the side frame members. Aligned with the central cavity 14 of the core 30 is a plunger 112 mounted to an advancing screw 114 threadedly journalled in the top member 116 of the frame 100. The advancing screw may be driven by a hand wheel 118 or by a suitable electric, hydraulic or pneumatic motor for moving the plunger 112 into and out of the cavity 14. The plunger 112 may be secured to the advancing screw 114 by means of a suitable connector assembly 120 which is also adapted to receive the probe 16 in place of plunger 112. The bottom plug 32, which is threadedly engaged in the cavity 14, may be secured to a hand wheel 122 for easy removal and insertion of the plug.

Figure 7:
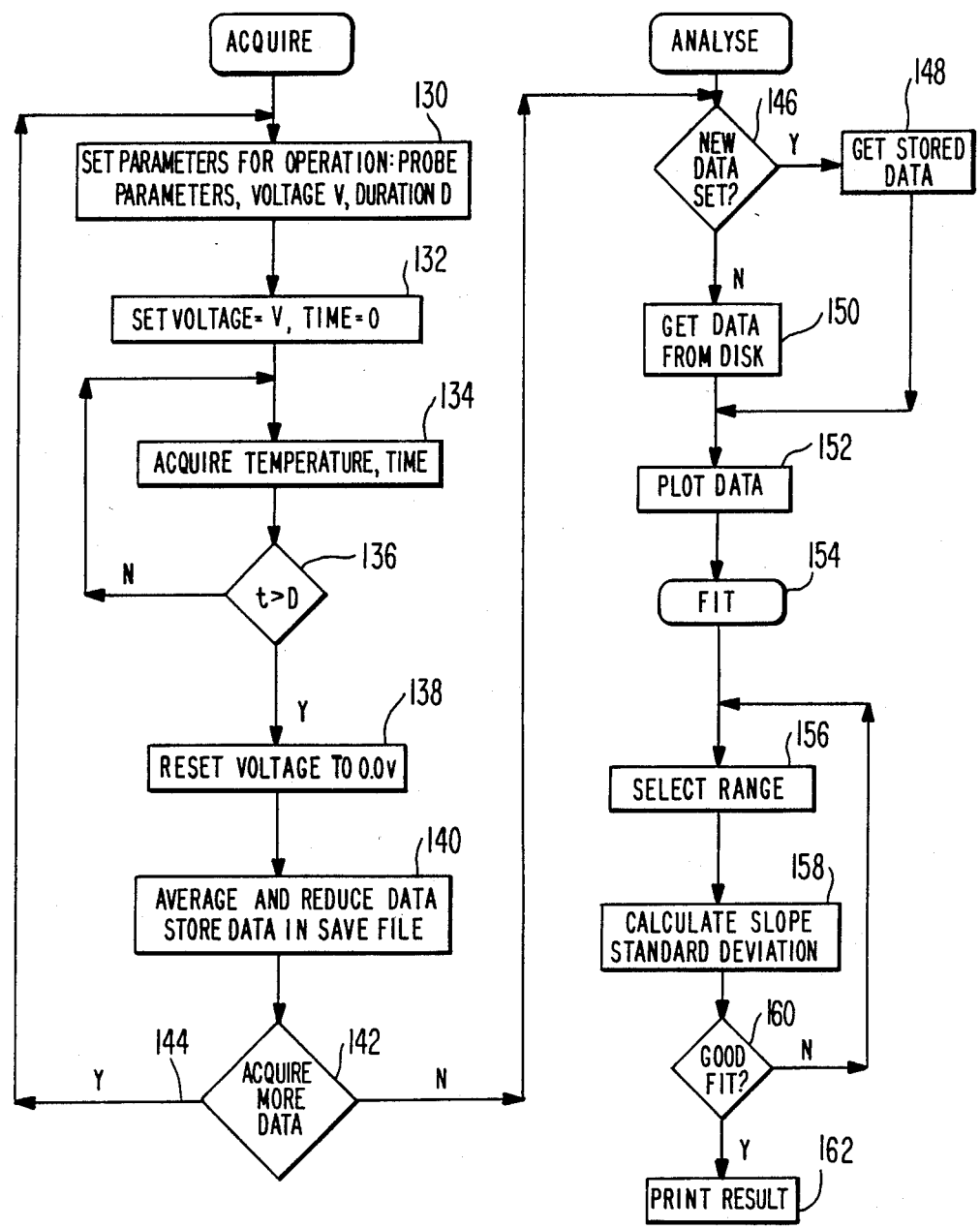
FIG. 7 is a flow chart of the operation of the system of the present invention.

In operation, the plug 32 is positioned in the bottom of cavity 14, and the sample material is placed in a cavity through the opening at the top of the sample heater. The plunger 112 is then advanced into the cavity by the advancing screw 114 to tamp the sample material in place as it is being heated so that the material will reach its desired melt temperature rapidly and without the formation of air bubbles. As the sample reaches its desired steady state temperature, the plunger is removed from the cavity and the probe is inserted therein either manually or by mounting it on the end of the advancing screw 114. The computer is then activated and, as illustrated in FIG. 7 at block 130, the parameters for operation of the device are established. Thus, the probe parameters, such as the voltage V to be applied to the transient heater, and the duration D for transient measurements, are selected. The voltage and time are then set, as illustrated in block 132, and the operation begins, with the computer acquiring temperature readouts from the probe over the selected time period, as shown at block 134. When the elapsed time is equal to the selected duration of measurement (block 136), the voltage applied to the transient heater is reset to zero (block 138), and the acquired data is averaged and stored, as indicated in block 140. The cycle may then be repeated, as indicated at block 142 and loop 144.

Upon completion of the desired number of cycles, the data is analyzed, for example by ploting the new data, as indicated by blocks 146, 148, 150 and 152, and the plotted data is used, as indicated by blocks 154, 156, 158 and 160, to calculate the slope of the transient curve to obtain a thermal conductivity value for the sample at the selected base temperature. The result is then printed, as indicated at block 162. Upon completion of the measurements of the sample material, the probe is removed from cavity 14, the plug 32 is removed, and the plunger 112 is replaced in the cavity and is pressed downwardly by the advancing screw 114 to discharge the sample material out the bottom opening of the cavity 14. This eliminates the tedious cleaning required with prior polymer melt testing equipment.

The thermal conductivity probe of the present invention works well on materials for which natural convection effects are negligible, such as liquids of high viscosity. Although there are no standards for this class of materials in the temperature range of interest; i.e., in the range of 200° to 400° C., the thermal conductivities for some materials are relatively well documented in the literature, thereby allowing comparative testing and calibration of the thermal conductivity measuring system 10. By comparing test results from the system 10 with prior well established values, a probe calibration constant is introduced into the relationship of equation 4. It was found that such a calibration constant reflected deviations of the actual hardware configuration from the idealized situation reflected in the foregoing equations, but since the constant had little or no temperature sensitivity, once established for a probe, the calibration constat permitted accurate measurements of thermal conductivity. Tests made with two liquid polymers, polyisobutylene and polydimethylsiloxane, and also for polypropylene and polystyrene generated thermal conductivity temperature profiles which agreed closely with data reported in the literature.

Thus, there has been disclosed a method and apparatus for measuring the thermal conductivity of polymer melts. Measurements on a wide range of commercial polymers, composites, and blends have revealed this technique to be an efficient method of measurement for such materials. Since the system provides a transient type of measurement, conductivity determinations can be made quickly before the effects of thermal degradation become apparent.

Although the present invention has been disclosed in terms of preferred embodiments thereof, variations and modifications will be apparent to those of skill in the art, and accordingly, the present invention is limited only by the following claims.

What is claimed is:

1. Apparatus for the measurement of polymer melts, comprising:
    an elongated cylindrical container for receiving a sample polymer material;
    sample heater means surrounding said container;
    temperature controller means energizing said sample heater means to heat a sample material in said container to a predetermined, initial, base temperature;
    probe means insertable into said container to contact sample material within the container, said probe means comprising:
    (a) an elongated, thin hollow needle secured at a near end to a probe connector housing and having its distal end sealed;
    (b) transient heater means within said needle and extending substantially the entire length thereof; and
    (c) temperature sensing means within said needle and substantially in contact with the wall of said needle;
    power supply means connected to said transient heater means and operable to energize said transient heater means to raise the temperature of a sample material surrounding said needle toward a temperature above said base temperature; and
    means connected to said temperature sensing means to measure the temperature of the probe to determine the change in temperature with time of a sample material in contact with the probe due to the energization of said transient heater means, whereby the thermal conductivity of a sample material in said container can be determined.

2. The apparatus of claim 1, wherein said sample heater means comprises a thermally conductive core and heater elements surrounding said core, and wherein said container comprises an elongated cavity formed in said core.

3. The apparatus of claim 2, wherein said cavity extends through said core to provide an inlet and an outlet, and further including removable plug means for said outlet.

4. The apparatus of claim 3, wherein said probe means is insertable into said cavity through said inlet.

5. The apparatus of claim 4, further including plunger means insertable into said cavity through said inlet to press sample material into the cavity prior to measurement of the temperature of the sample material, and to thereafter discharge sample material from said outlet.

6. The apparatus of claim 5, further including temperature display means connected to said temperature sensing means.

7. The apparatus of claim 1, wherein the heat supplied to said sample by said transient heater means is relatively small compared to the heat supplied by said sample heater means.

8. The apparatus of claim 7, wherein energization of said power supply means connected to said transient heater means produces a transient temperature field which penetrates said sample to a radial distance on the order of 0.1 cm from said probe means.

9. The apparatus of claim 8, wherein said probe has a length-to-diameter ratio greater than 20.

10. The apparatus of claim 9, wherein said sample heater means includes a thermally conductive core and heater means for heating said core, and wherein said container is located in and is substantially surrounded by, said core.

11. The apparatus of claim 10, wherein said container extends through said core to provide a container inlet and a containr outlet, said container inlet receiving said probe means, and said container outlet including removable plug means.

12. The apparatus of claim 11, further including means supplying pressure to a sample in said container.

13. The apparatus of claim 1, wherein said temperature sensing means is located substantially midway along the length of said needle.

14. The apparatus of claim 1, wherein said container is a cavity formed in said sample heating means.

15. The apparatus of claim 1, wherein said sample heater means comprises a thermally conductive bath and heater elements for heating said bath, and wherein said container comprises vial means mountable in said bath.

16. The appatus of claim 1, further including means mounted on said container for supplying pressure to said sample material during measurement thereof.

17. A method of measuring the thermal conductivity of a polymer melt, comprising:
placing a sample polymer material in an elongated cylindrical container;
positioning the container in a sample heater;
energizing said sample heater to heat said sample material in said container to a predetermined, stable base temperature at or above the melting temperature of said sample material;
inserting an elongated, thin measuring probe including a transient heater and a temperature sensor into said sample material;
stabilizing the temperature of said measuring probe at said base temperature;
energizing said transient heater in said probe to increase the temperature of the sample material surrounding said probe from said base temperature toward a second, higher temperature;
measuring the temperature of the sample material in contact with said probe to obtain a temperature profile of the sample material during a time of transient temperature change in the sample material; and
determining from said temperature profile the thermal conductivity of said sample material.

18. The method of claim 17, wherein said transient heater is energized for a time period sufficient to produce a transient temperature field which penetrates said sample to a radial distance on the order of 0.1 cm from said probe.

19. The method of claim 18, wherein said transient heater is energized to supply a sufficiently small amount of heat the sample to enable the sample to rapidly return to its base temperature upon deenergization of the transient heater.

20. The method of claim 17, wherein said transient heater is energized for a time period of less than about 30 seconds, whereby the thermal conductivity of said sample material is determined from a temperature transient in said sample material.

21. The method of claim 17, wherein said transient heater is deenergized upon completion of the measurements required to obtain a temperature profile, and said sample material is allowed to return to said base temperature to complete a cycle of measurement, and thereafter repeating said cycle of measurement.

22. The method of claim 17, further including applying pressure to said sample during measurement of the temperature thereof.

* * * * *